(12) United States Patent
Zhou et al.

(10) Patent No.: US 8,489,202 B2
(45) Date of Patent: *Jul. 16, 2013

(54) ADHERENT METAL OXIDE COATING FORMING A HIGH SURFACE AREA ELECTRODE

(75) Inventors: Dau Min Zhou, Saugus, CA (US); Robert J. Greenberg, Los Angeles, CA (US); Neil H. Talbot, Montrose, CA (US)

(73) Assignee: Second Sight Medical Products, Inc., Sylmar, CA (US)

(*) Notice: Subject to any disclaimer, the term of this patent is extended or adjusted under 35 U.S.C. 154(b) by 606 days.

This patent is subject to a terminal disclaimer.

(21) Appl. No.: 11/489,777

(22) Filed: Jul. 19, 2006

(65) Prior Publication Data

US 2006/0259109 A1 Nov. 16, 2006

Related U.S. Application Data

(62) Division of application No. 10/655,772, filed on Sep. 5, 2003, now Pat. No. 7,571,011.

(60) Provisional application No. 60/467,789, filed on May 1, 2003.

(51) Int. Cl.
*A61N 1/04* (2006.01)

(52) U.S. Cl.
USPC ............................ 607/115; 607/54; 607/121

(58) Field of Classification Search
USPC ........................... 607/115, 54, 121
See application file for complete search history.

(56) References Cited

U.S. PATENT DOCUMENTS

| 3,424,617 | A | * | 1/1969 | Jaffe et al. ..................... 429/58 |
| 4,240,878 | A | | 12/1980 | Carter |
| 4,331,528 | A | * | 5/1982 | Beer et al. ................. 204/290.08 |
| 4,426,262 | A | * | 1/1984 | Langley et al. ............... 205/535 |
| 4,510,034 | A | * | 4/1985 | Ohshima et al. ............. 204/284 |
| 5,109,844 | A | | 5/1992 | de Juan, Jr. et al. |
| 5,318,572 | A | * | 6/1994 | Helland et al. ............... 607/121 |
| 5,571,158 | A | | 11/1996 | Bolz et al. |
| 5,609,611 | A | | 3/1997 | Bolz et al. |
| 5,632,770 | A | | 5/1997 | Schaldach |
| 5,683,443 | A | * | 11/1997 | Munshi et al. ............... 607/121 |
| 5,822,177 | A | | 10/1998 | Popp et al. |
| 5,871,511 | A | | 2/1999 | Bolz et al. |
| 5,935,155 | A | | 8/1999 | Humayun et al. |

(Continued)

OTHER PUBLICATIONS

Am Feltham, et al.; Platinized Platium Electrodes. Chemical Reviews, 1971; pp. 177-193; vol. 71; No. 2; Dept of Chem, Imperial College of Sci and Tech, London SW7, England.

(Continued)

*Primary Examiner* — Niketa Patel
*Assistant Examiner* — Christopher A Flory
(74) *Attorney, Agent, or Firm* — Scott B. Dunbar; Alessandro Steinfl; Gary Schnittgrund

(57) ABSTRACT

An implantable electrode having a strong, adherent surface coating of iridium oxide or titanium nitride on a platinum surface, where the platinum surface has a surface area of at least five times that of a smooth shiny platinum surface of the same geometry. The iridium oxide coating may be formed on platinum by a physical deposition process, such as sputtering. A gradient coating of iridium oxide ranging in composition from pure platinum to pure iridium oxide is produced by sputtering.

10 Claims, 5 Drawing Sheets

U.S. PATENT DOCUMENTS

| | | | |
|---|---|---|---|
| 5,964,794 A | 10/1999 | Bolz et al. | |
| 6,040,077 A * | 3/2000 | Debe et al. | 429/524 |
| 6,219,581 B1 | 4/2001 | Schaldach et al. | |
| 6,230,061 B1 | 5/2001 | Hartung | |
| 6,292,703 B1 | 9/2001 | Meier et al. | |
| 6,324,429 B1 * | 11/2001 | Shire et al. | 607/54 |
| 6,400,989 B1 | 6/2002 | Eckmiller | |
| 6,430,448 B1 * | 8/2002 | Chitre et al. | 607/121 |
| 6,458,157 B1 | 10/2002 | Suaning | |
| 6,522,924 B1 | 2/2003 | Meier | |
| 6,546,292 B1 * | 4/2003 | Steinhaus et al. | 607/116 |
| 6,805,788 B1 * | 10/2004 | Gonzalez-Martin et al. | 205/775.5 |
| 6,974,533 B2 * | 12/2005 | Zhou | 205/264 |
| 7,047,080 B2 * | 5/2006 | Palanker et al. | 607/54 |
| 7,571,011 B2 * | 8/2009 | Zhou et al. | 607/116 |
| 7,887,681 B2 * | 2/2011 | Zhou | 204/292 |
| 8,200,338 B2 * | 6/2012 | Grennberg et al. | 607/53 |
| 2005/0271895 A1 * | 12/2005 | Zhou | 428/670 |

OTHER PUBLICATIONS

M. Schaldach; Fractal Coated Leads: Advanced Surface Tech for Genuine Sensing and Pacing; Prog in Biomedical Research, Jun. 2000; pp. 259-272; Dept. of Biomed Eng; Germany.

"Platinized Platium Electrodes", A.M. Feltham and M. Spiro, Department of Chemistry, Imperial College of Science and Technology, London S.W.7, England; Chemical Reviews, 1971, vol. 71, No. 2; pp. 178-193.

"Fractal Coated Leads: Advanced Surface Technology of Genuine Sensing and Pacing", M. Schaldach, Department of Biomedical Engineering, Erlangen-Nuremberg, Germany Progress in Biomedical Research, Jun. 2000; pp. 259-272.

* cited by examiner

ADHERENT METAL OXIDE COATING FORMING A HIGH SURFACE AREA ELECTRODE

CROSS REFERENCE TO RELATED APPLICATION

This application is a divisional application of U.S. application Ser. No. 10/655,772, now U.S. Pat. No. 7,571,011 issued on Aug. 4, 2009 to Zhou, et al., which claims the benefit of U.S. Provisional Application Ser. No. 60/467,789, filed on May 1, 2003, the disclosures of all of which are incorporated herein by reference.

FEDERALLY SPONSORED RESEARCH

This invention was made with government support under grant No. R24EY12893-01, awarded by the National Institutes of Health. The government has certain rights in the invention.

FIELD OF THE INVENTION

This invention relates to metal oxide forming an adherent high surface area coating on an electrode surface.

BACKGROUND OF THE INVENTION

It has been known for 200 years that muscle contraction can be controlled by applying an electrical stimulus to the associate nerves. Practical long-term application of this knowledge was not possible until the recent development of totally implantable miniature electronic circuits that avoid the risk of infection at the sites of percutaneous connecting wires. One example of this modern technology is the cardiac pacemaker.

A metal of choice in electrode manufacturing has traditionally been titanium. On a fresh titanium surface, however, oxygen ions react with the titanium anode to form an oxide layer. Once a finite oxide thickness has been formed on the surface, polarization increases. The oxide film developed on the surface of a titanium electrode is irreversible. It cannot be reduced to the original metal by passing a charge in the reverse direction. Hence, pure titanium metal is a poor choice for electrodes since it forms a semi-conductive oxide on its surface before and during electrical stimulation. Platinum and stainless steel undergo irreversible dissolution during stimulation as well.

Titanium oxidation reactions are several times more likely in an oxidative environment than those of platinum or platinum alloys, but a thousand times less so than those of stainless steel. Due to the expense of platinum metal and the requirement for large amounts of metal in patch-type electrodes, costs may be too high for the routine use of platinum electrodes.

The charge storage capacity, C, is calculated according to the equation $C=(k)(\epsilon)(A/d)$, where k is the dielectric constant of the film, $\epsilon$ is the permissivity in vacuum, A is the true surface area of the film, and d is the thickness of the porous material, it can be seen that in order to achieve a large charge storage capacity (C), the porosity of the dielectric may be maximized with a large film surface area. Numerous types of cardiac pacing and defibrillation electrodes have been developed with these factors in mind, utilizing various configurations and materials asserted to promote lower stimulation thresholds and to improve electrical efficiencies. Thus, for implantable electrode applications, it is desirable to minimize the electrical impedance at the electrode-tissue interface by increasing the intrinsic surface area of the electrode or by reducing formation of the capsule of inactive tissue that surrounds and isolates the electrode from living tissue. Schaldach discusses in detail the selection criteria for implantable electrodes. See M. Schaldach, "Fractal Coated Leads: Advanced Surface Technology for Genuine Sensing and Pacing," Progress in Biomedical Research, 259-272, June 2000.

Microporous electrodes based on sintered titanium, sintered titanium nitride, and microporous carbon or graphite have been used with some degree of success. However, the electrode reactions in aqueous solutions involve significant gas generation similar to the behavior of titanium. Abrading or sandblasting electrode surfaces is a broadly used method to achieve surface area enhancement. For example, French Patent No. 2,235,666 relates to a stainless steel electrode tip that is sanded to increase surface area and reduce the impedance of the electrode.

Other methods have also been used. U.S. Pat. No. 5,318,572 relates to a 90% platinum-10% iridium porous electrode with recess slots in the shape of a cross and at least one, preferably two variably-sized, porous coatings of 20 to 80 micron diameter 90% platinum-10% iridium spheres deposited on the surface of the electrode. On top of this structure, a reactively sputtered coating of titanium nitride was applied. U.S. Pat. No. 4,156,429 describes a means for increasing the reactive surface area by forming a highly porous sintered electrode body consisting of a bundle of fibers, preferably of platinum but alternatively of ELGILOY, titanium, or a platinum-iridium alloy. Conversely, the fibers may be encompassed within a metallic mesh to yield 70% to 97% porosity. U.S. Pat. No. 5,203,348 relates to defibrillation electrodes that can be formed on titanium ribbons or wires with a sputtered outer layer of platinum, or a silver core in a stainless steel tube with a platinum layer formed onto the tube. U.S. Pat. No. 5,230,337 discloses that the coating is preferably made by sputtering to increase the surface area of the electrode.

U.S. Pat. No. 5,178,957 relates to electrodes and a method of making electrodes including pretreatment of the surface by sputter-etching and sputter-depositing a noble metal on the surface. U.S. Pat. No. 5,074,313 relates to a porous electrode with an enhanced reactive surface wherein surface irregularities are introduced to increase surface area by glow discharge or vapor deposition upon sintered wires. U.S. Pat. No. 4,542,752 describes a platinum or titanium substrate coated with a porous sintered titanium alloy that in turn is coated with a porous carbon. The latter was claimed to promote tissue ingrowth and provide low polarization impedance. U.S. Pat. No. 4,784,161 relates to making a porous pacemaker electrode tip using a porous substrate, where the porous substrate is preferably a non-conductive material such as a ceramic or a polymer made porous by laser drilling, sintering, foaming, etc. to result in pores 5 to 300 microns in depth. U.S. Pat. No. 4,603,704 features a hemispherical electrode made of platinum or titanium, coated with a porous layer consisting of a carbide, nitride, or a carbonitride of at least one of the following metals: titanium, hafnium, molybdenum, niobium, vanadium, or tungsten. U.S. Pat. No. 4,281,668 discloses a vitreous carbon or pyrolytic carbon electrode that is superficially activated, e.g., by oxidation, for microporosity. The electrode is then coated with a biocompatible ion-conducting, hydrophobic plastic.

Despite the numerous means of increasing the surface area to reduce polarization losses and after potentials and the use of noble metals and their alloys as electrodes as described above, with varying degrees of success, there remain significant problems pertaining to polarization losses and sensing difficulties. In order to make further improvements to the electrode, stable oxides of some of these noble metals have been employed as a coating.

It is known that certain metals, metallic oxides, and alloys are stable during electrolysis, and that these metals are useful in a variety of electrode applications, such as chlor-alkali electrolysis (see U.S. Pat. No. 5,298,280). Such metals typically include the elements of the platinum group; namely, ruthenium, rhodium, palladium, osmium, iridium, and platinum. These metals are not suitable for construction of the entire electrode, since their cost is prohibitive. Therefore, these metals or their alloys, or as metallic oxides, have been applied as a thin layer over a base member made of Ti, Ta, Nb, Hf, Zr, or W. These metals are much less expensive than platinum group metals and they have properties that render them corrosion resistant. However, as previously mentioned, they lack good surface electroconductivity because of their tendency to form a surface oxide having poor electroconductivity.

U.S. Pat. No. 5,683,443 discloses implantable stimulation electrodes for living tissue stimulation where the titanium electrodes have metal oxides, such as iridium oxide, applied as coatings on an electrode surface, where the surface area has been increased by mechanical shaping, abrasion by sandblasting, or roughening by chemical etching. The patent also discloses surface area enhancement by applying coatings of metal oxides by virtue of the preferred fit which is possible using mixed sized metal oxide molecules in a lattice arrangement. Thus, a single metal oxide produces a mono-lattice with gaps, but a mixed metal oxide with differently sized molecules produces a binary lattice where the gaps of the mono-lattice may be filled by the smaller of the two molecules.

Iridium oxide may be used as a protective coating for metallic electrodes made of platinum, platinum iridium alloy, stainless steel, stainless steel alloys, titanium, titanium alloys, tantalum, or tantalum alloys. U.S. Pat. No. 4,677,989 discloses a metallic electrode that is made of a metal other than iridium that is coated with iridium oxide to reduce corrosion and to increase charge capacity while being thin, thus allowing charge to flow to living tissue from the electrode. Formation of an iridium oxide coating by a solution chemistry deposition process is discussed.

U.S. Pat. No. 5,632,770 discloses an implantable device with a porous surface coating having an active surface that is substantially larger than the geometric shape of the electrode. The enhanced surface area was achieved by a three dimensional fractal-like geometry that increased the surface area by 1000 fold. A coating such as iridium nitride or iridium oxide applied by vacuum technology, particularly vapor deposition, such as reactive cathode sputtering, CVD, PVD, MOCVD, or ion plating is disclosed.

Electroplated or sputtered iridium oxide on a metal surface cracks and delaminates after a short period of electric current pulsing. Thermo-prepared iridium oxide has no such problem. Some commercially available pacemaker leads lasted for eight years of implantation. It is believed that thermo-prepared iridium oxide has better adhesion to the substrate (usually Ti). High temperature will fuse the iridium oxide coating to the substrate. However, since this process requires high temperature, it is not compatible with materials that are high temperature sensitive.

EIC Laboratories of Norwood, Mass. electroplated iridium oxide on a machined surface of a solid disk of platinum and electroplated iridium oxide on a highly polished thin film of platinum; both had low adhesion strength. Some electrodes had delamination of iridium oxide with static exposure at room temperature to 10% saline. Some electrodes developed cracks after a few voltage cycles (i.e., cyclic voltammetry) −0.6V to +0.8V. The plated layer appears dense and smooth. Sputtered iridium or iridium oxide exhibits the same limitations.

U.S. patent application Ser. No. 10/226,976, titled "Platinum Electrode and Method for Manufacturing the Same," to Zhou, now U.S Pat. No. 6,974,533, discloses an alternative fractal platinum material and methods of manufacture and is incorporated herein by reference in its entirety. Due to the superior electrical characteristics of platinum as well as its biocompatibility and stability, platinum is a preferred material for electrodes in harsh environments, such as in a human body. However, because electrodeposited platinum, also called "bright platinum", has a smooth surface when deposited at a slow deposition rate, its surface area is limited by the geometry of the electrode, and therefore, it is not efficient for transferring electrical charge.

Another form of platinum, known as "platinum black," is widely known. It is deposited at a high rate and demonstrates high porosity, low strength, a rough surface that has lower bulk density, and less reflectivity of visible light than bright platinum. U.S. Pat. No. 4,240,878 describes a method of plating platinum black.

Platinum black may require additives, such as lead, which promote rapid plating. Lead, however, is a neurotoxin and cannot be used in biological systems. Because platinum black is weak, the thickness of the electroplated layer is quite limited. Thick layers of platinum black are inherently weak and readily flake.

Another form of platinum is "platinum gray," which possesses intermediate properties between those of bright platinum and platinum black. Formed by electrodeposition at an intermediate rate between that utilized for bright platinum and platinum black, it possesses the desirable high surface area that is characteristic of its fractal morphology. It is strong and can be deposited in thick layers on implantable electrodes. However, it suffers from long-term degradation when exposed to living tissue and when subjected to higher charge density stimulation.

It is desired to have the benefit of a high surface area electrode that is comprised of porous platinum and that is coated with an inert, strong coating that vigorously adheres to the substrate and therefore does not flake off during long-term exposure to living tissue.

SUMMARY OF THE INVENTION

This invention is directed to an implantable, coated electrode having high surface area for greater ability to transfer charge and also having sufficient physical and structural strength to withstand physical stresses encountered during use.

This and other aspects of the present invention which may become obvious to those skilled in the art through the following description of the invention are achieved by a coated electrode and method for manufacturing the electrode wherein the electrode has a fractal surface coating of platinum, known as "platinum gray," with a increase in surface area of at least 5 times when compared to shiny platinum of the same geometry and also having improved resistance to mechanical stress when compared to platinum black. The platinum gray fractal surface is coated with either a gradient or discrete coating of an inert material, such as iridium oxide.

The novel features of the invention are set forth with particularity in the appended claims. The invention will be best understood from the following description when read in conjunction with the accompanying drawings.

DETAILED DESCRIPTION OF THE PREFERRED EMBODIMENT

Figure 1:
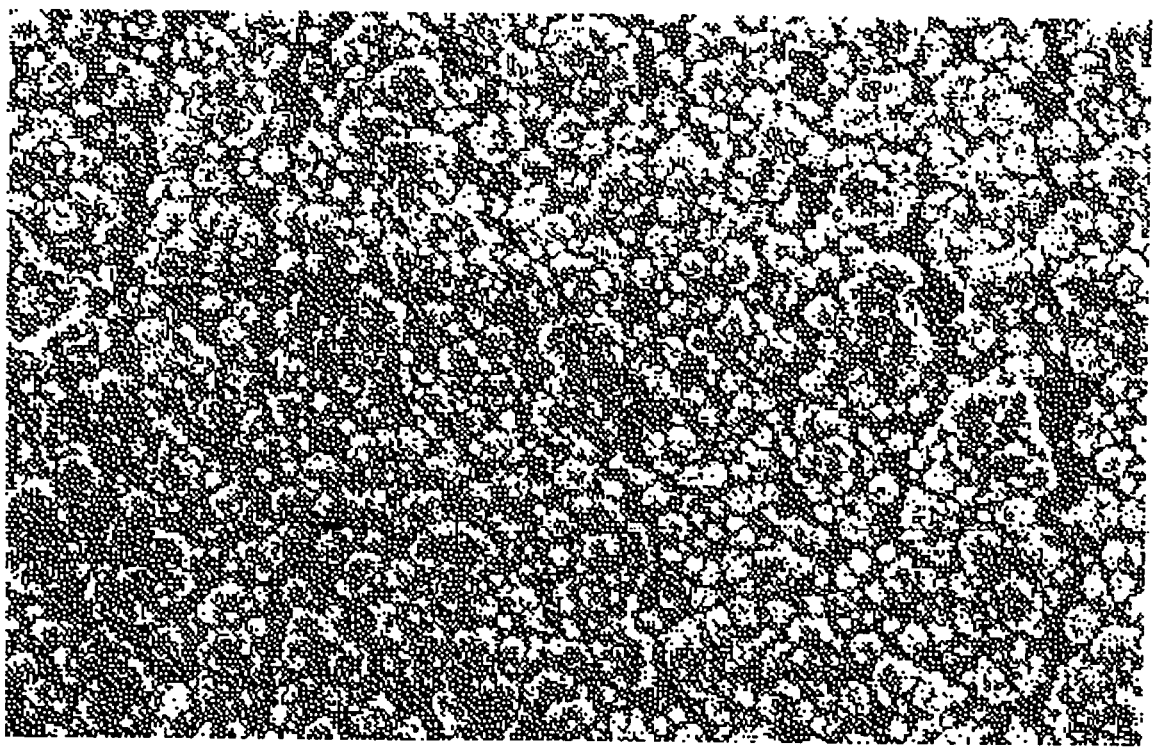
FIG. 1 presents a scanning electron micrograph of iridium oxide deposited on a platinum gray surface.

Referring to FIG. 1, an illustrative example of an iridium oxide coating on a platinum gray surface of an electrode, according to the present invention, is shown having a fractal surface with a surface area increase of between 5 and 500 times the surface area for a shiny platinum surface of the same size. An implantable electrode and method for manufacturing the electrode wherein the electrode has a strong adherent surface coating of iridium oxide or titanium nitride on a platinum surface, which demonstrates an increase in surface area of at least five times when compared to smooth platinum of the same geometry. The iridium oxide coating may be formed on platinum by a physical deposition process. such as sputtering. The process of electroplating the iridium oxide surface coating is accomplished by voltage control processes. A gradient coating of iridium oxide ranging in composition from essentially pure platinum to essentially pure iridium oxide is produced by sputtering. An implantable electrode comprising a roughened conductive substrate: and a rough surface coating on the substrate. The implantable electrode, wherein said surface coating has a surface area of between 5 and 500 times the corresponding surface area resulting from the basic geometric shape.

The implantable electrode, wherein the surface coating is comprised of iridium oxide. The implantable electrode has a charge storage capacity that is greater than 35 mC/cm$^2$. The implantable electrode, where the surface coating is comprised of titanium nitride.

The implantable electrode, wherein the titanium nitride is a sputtered coating. The implantable electrode. wherein the surface coating is comprised of a graded coating. The implantable electrode, wherein the graded coating is comprised of platinum gray and iridium oxide.

The implantable electrode, wherein the electrode is suitable for a visual prosthesis. The implantable electrode, wherein the visual prosthesis is a retinal electrode array.

The implantable electrode, wherein the roughened conductive substrate is comprised of platinum gray.

The implantable electrode, wherein the surface coating is biocompatible.

The implantable electrode, wherein the surface coating has a thickness of at least 1 micron. The implantable electrode, wherein the surface coating has a thickness of less than 1 micron.

The implantable electrode, wherein at least a portion of the surface coating has fractal morphology. The implantable electrode, wherein at least a portion of said roughened conductive substrate is comprised of a fractal morphology.

The implantable electrode, wherein the surface coating is a sputtered coating. The implantable electrode, wherein the roughened conductive substrate is comprised of a fractal morphology. The implantable electrode. wherein the surface coating is an electroplated coating.

Figure 2:
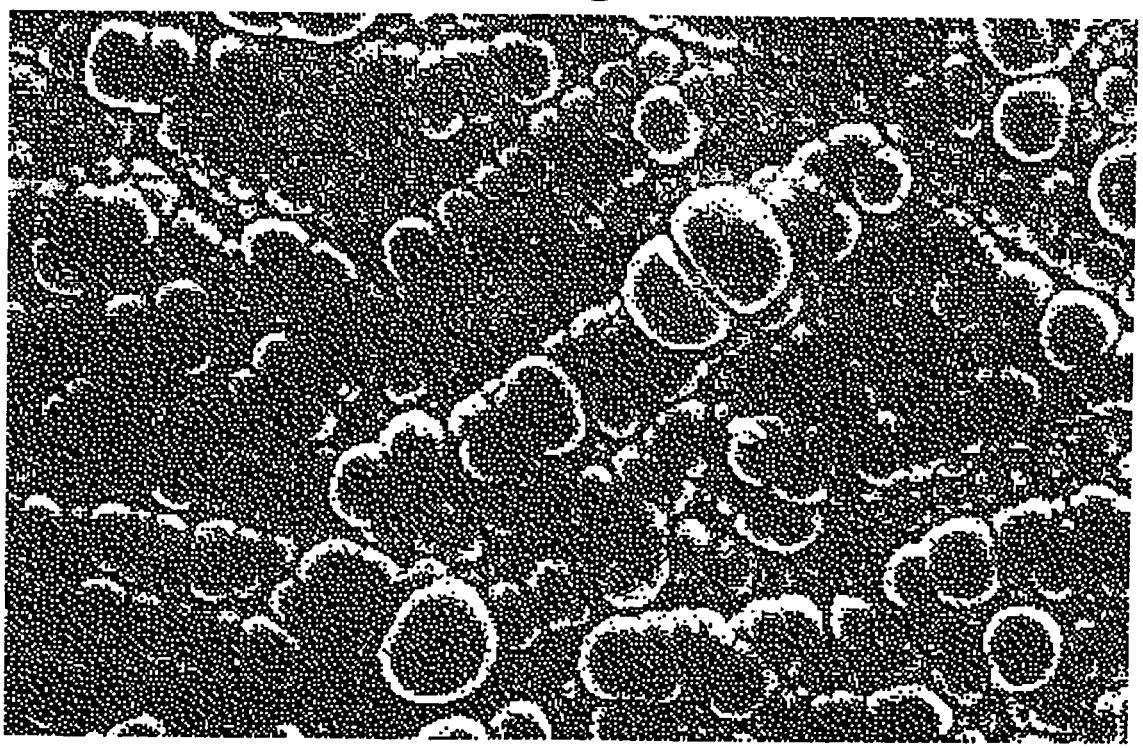
FIG. 2 presents a scanning electron micrograph of iridium oxide deposited on a rough platinum surface.

The implantable electrode. wherein the surface coating is comprised of electroplated iridium oxide and the conductive substrate is comprised of platinum gray. FIG.2 presents a scanning electron photomicrograph of a rough platinum surface that is coated with iridium oxide. It is clear that the electrode surface may, in an alternative embodiment, be a rough surface that is achieved on a surface such as platinum, which has been roughened by abrasion, such as by abrasion blasting or chemical etching. FIGS. 1 and 2 are scanning electron micrographs taken on a JEOL JSM5910 scanning electron microscope. Iridium oxide coats the fractal surface of the platinum gray with a cauliflower-like morphology with feature sizes ranging from 0.5 to 15 microns. Each branch of such structure is further covered by smaller and smaller features of similar shape. The features particles on the surface layer may be in the nanometer range. This rough and porous fractal structure increases the electrochemically active surface area of the platinum surface when compared to an electrode with a smooth platinum surface having the same geometric shape.

Because no impurities or other additives, such as lead, which is a neurotoxin and cannot be used in an implantable electrode, need to be introduced during the plating process to produce platinum gray, the surface is essentially pure platinum.

Figure 7:
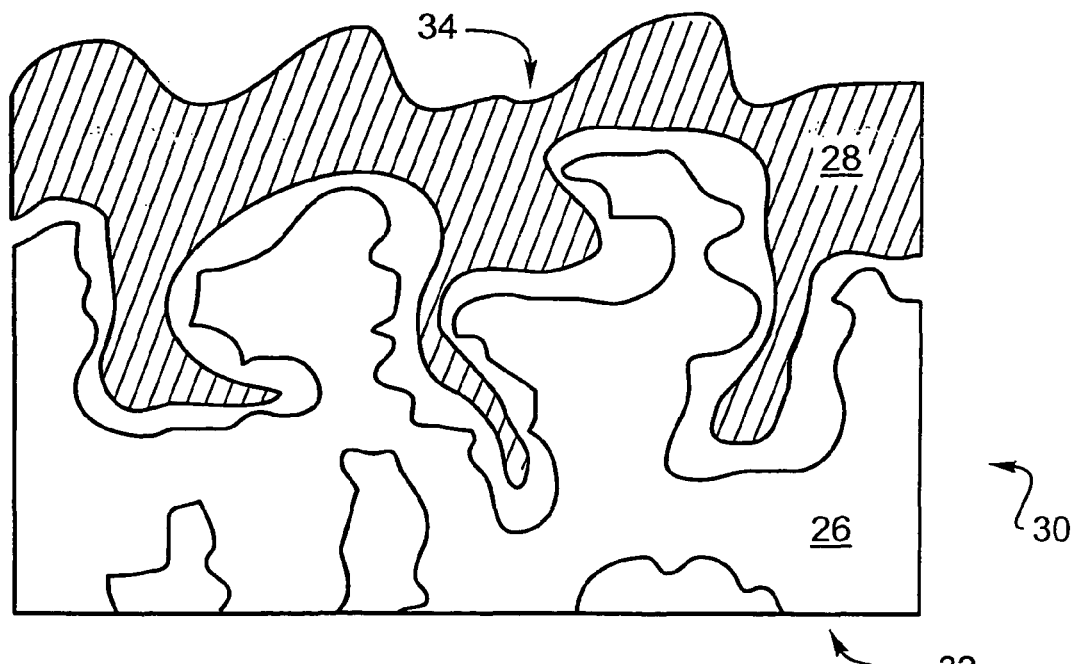
FIG. 7 illustrates the formation of a gradient coating in cross-section.

A quasi-gradient coating 30 is achieved by plating iridium oxide 28 on the extremely porous surface of platinum gray 26, as illustrated in FIG. 7. The average coating composition increases from pure platinum to pure iridium oxide as one moves from the bottom surface 32 to the top surface 34 of the sample. The resulting iridium oxide coating is very adherent to the platinum gray base material (not illustrated).

Platinum gray can also be distinguished from platinum black based on the adhesive and strength properties of the thin film coating of the materials. Adhesion properties of thin film coatings of platinum gray and platinum black on 500 microns diameter electrodes were measured on a Micro-Scratch Tester (CSEM Instruments, Switzerland). A controlled microscratch was generated by drawing a spherical diamond tip of radius 10 microns across the coating surface under a progressive load from 1 to 100 millinewtons with a 400 micron scratch length. At a critical load the coating stared to fail. It was found that platinum gray had a critical load of over 60 millinewtons while platinum black had a critical load of less than 35 millinewtons.

The platinum gray layer is introduced as an adhesion layer between metal substrate and iridium oxide. This mid-layer is micro-rough and micro-porous which provides at least two benefits: (a) larger surface area due to its fractal structure to accommodate more iridium oxide mass in a less dense form; and (b) providing a rough surface for iridium oxide deposition and promote good adhesion to substrate. The iridium oxide coating on such modified surface is less dense and has better adhesion. This iridium oxide layer provides very high charge storage capacity for pulse stimulation. The electrode can also be used as electrochemical sensors. This mid-layer is introduced by electroplating platinum or other metals such as iridium, rhodium, palladium, gold, tantalum, titanium, niobium or their alloys.

Other surface modification techniques (such as chemical, electrochemical and physical etching, low temperature thin-film deposition methods, etc.) can also be used to provide a rough surface for iridium oxide plating.

Figure 3:
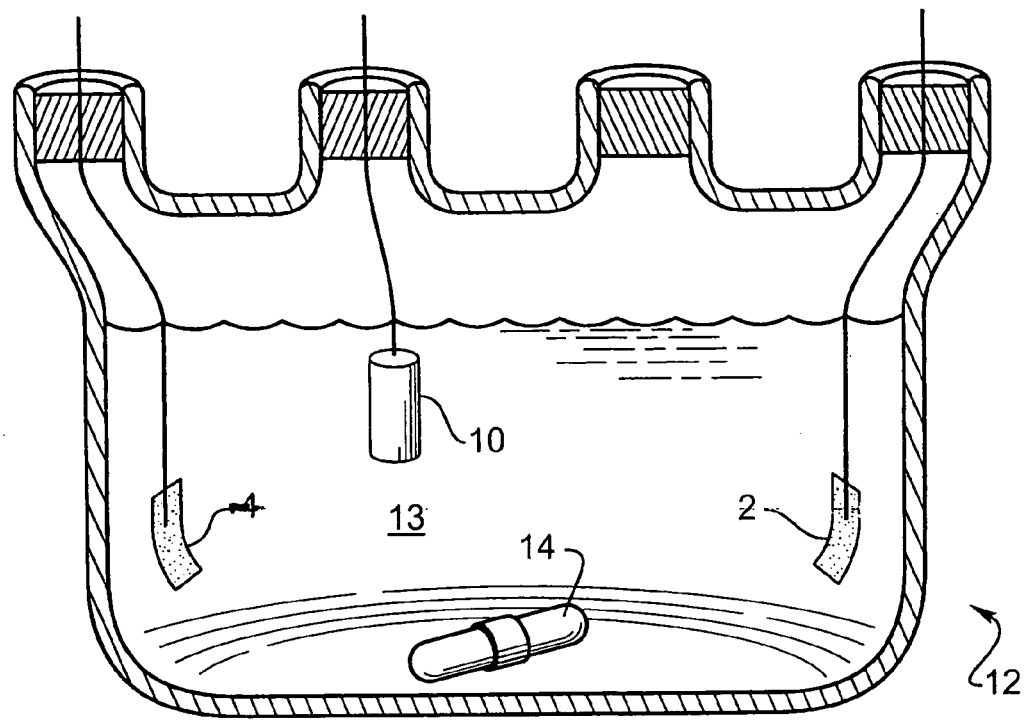
FIG. 3 is a three-electrode electroplating cell with a magnetic stirrer.
Figure 4:
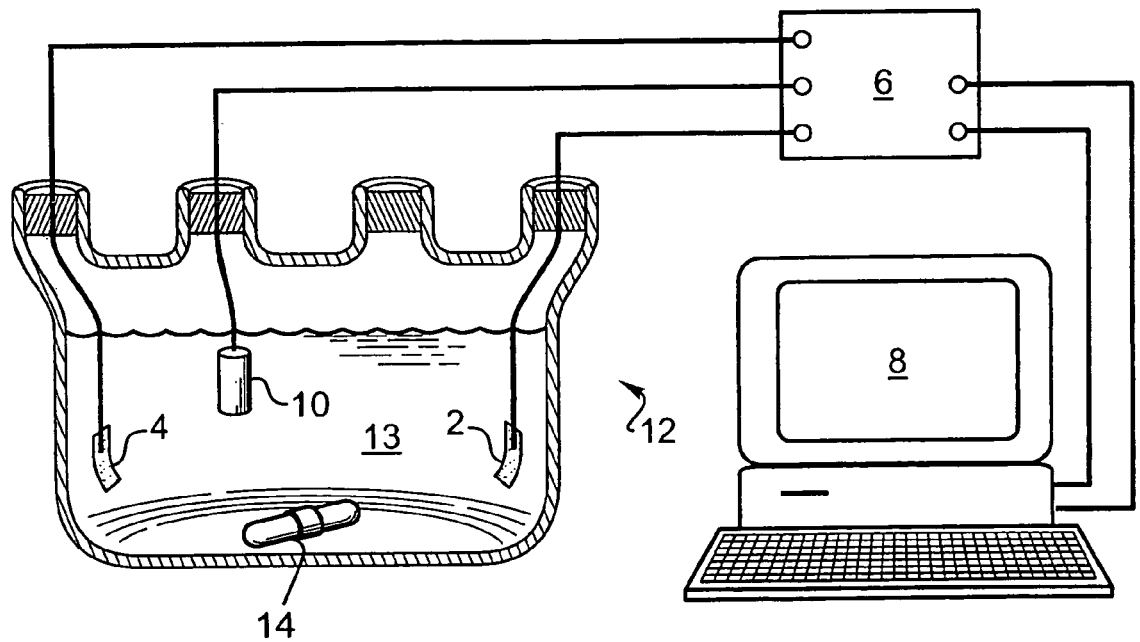
FIG. 4 is an electroplating system with constant voltage control or scanned voltage control.

Referring to FIGS. 3 and 4, a method to produce adherent iridium oxide according to the present invention is described, comprising an electroplating cell 12, generally, connecting a common electrode 2, which is preferably comprised of platinum, and a working electrode 4 to be plated The working electrode 4 (which is the cathode during platinum gray plating and is the anode during iridium oxide plating) is connected to a potentiostat 6, which is the power source, with a computer monitor 8, for control and process monitoring of either the current or voltage of the potentiostat 6. The common electrode 2, working electrode 4, reference electrode 10 for use as a reference in controlling the potentiostat 6 and electroplating solution 13 are placed in an electroplating cell 12 having a means for mixing or agitating 14 the electroplating solution 13. Electrical power is supplied to the electrodes with a constant voltage or a scanned voltage to drive the electroplating process. Referring to FIG. 3, the electroplating cell 12, is preferably a 30 ml to 150 ml four-neck glass flask or beaker, the common electrode 2, is preferably a large surface area platinum wire or platinum sheet, the reference electrode 10 is preferably a Ag/AgCl electrode (silver, silver chloride electrode), the working electrode 4 that is to be plated, can be any suitable material depending on the application and can be readily chosen by one skilled in the art. Preferable examples of the working electrode 4 to be plated include but are not limited to platinum, iridium, rhodium, gold, tantalum, titanium, niobium or their alloys. The plated iridium oxide is dark blue in color.

The means for mixing or agitating 14 is preferably a magnetic stirrer, as shown in FIG. 3. The plating solution 13 is preferably 3 to 6 mM (millimole) iridium chloride in potassium carbonate solution buffered to a pH of 10-11. The preferable plating temperature is approximately 24° C. to 26° C.

An electroplating system with constant voltage and scanned voltage control is shown in FIG. 4. While, constant current, pulsed voltage or pulsed current can be used to control the electroplating process (such as a pulsed, rectangular potential waveform between 0.0V and 0.55V vs. saturated calomel electrode (SCE), with a 0.2 to 5 second dwell at each limit), constant voltage control of the plating process has been found to be most preferable. The most preferable voltage range to produce adherent iridium oxide has been found to be +0.45V to +0.65V. Applying voltage in this range with the above solution 13 yields a plating rate of about 2 to 4 $mC/cm^2$/min, which is the preferred range for the plating rate of iridium oxide. Constant voltage control also allows an array of electrodes to be plated in parallel simultaneously, achieving the same surface layer thickness for each electrode.

A constant voltage is applied on the common electrode 2 as compared to the reference electrode 10 preferably using an EG&G PAR M273 model potentiostat 6. The response current of the common electrode 2 is recorded by a the computer monitor 8. After a specified time, preferably 15-90 minutes, and most preferably 30 minutes, the voltage is turned off and the working electrode 4 is thoroughly rinsed in deionized water.

The electrochemical impedance of the electrode array with the surface coating of platinum gray is measured in a saline solution. The charge/charge s density and average plating current/current density are calculated by integrating the area under the plating current as a function of time curve. Scanning Electron Microscope (SEM) Energy Dispersive X-ray Analysis is performed on selected electrodes. SEM micrographs of the plated surface are taken showing the fractal surface morphology. Energy Dispersive X-ray Analysis demonstrates that the sample consists of platinum and iridium oxide.

Figure 5:
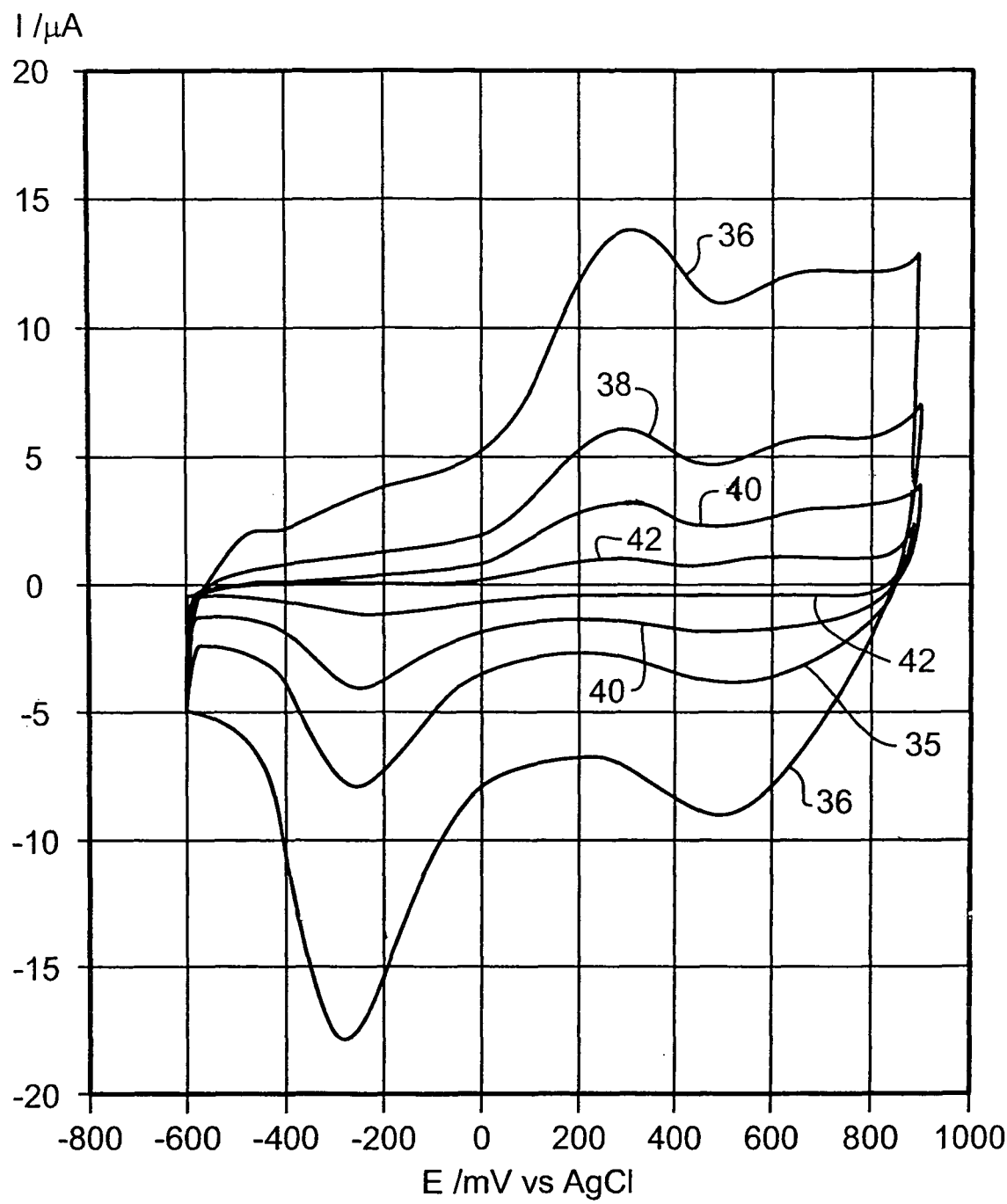
FIG. 5 is cyclic voltammograms of electroplated iridium oxide.

Cyclic voltammetry and Electrochemical Impedance Spectroscopy in PBS (0.126 M NaCl, 0.1 M $NaH_2PO_4$/$Na_2HPO_4$ at pH=7.2) saturated with argon or nitrogen measures the charge storage capacity of the iridium oxide electrodes. FIG. 5 presents the cyclic voltammograms of an iridium oxide plated microelectrode array. The electrodes have four different sizes with 500, 350, 250 and 150 μm diameter thin-film platinum disks coated with iridium oxide on platinum gray. Two pairs of current peaks within the potential range of −0.6V to +0.8V, are presented on the voltammograms, FIG. 5, are typically observed for iridium oxide reduction and oxidation reactions. The charge storage capacity, calculated by integrating the area under the voltammograms, has an average value of 102 $mC/cm^2$ (115, 103, 100 and 91 $mC/cm^2$ for the four different electrode sizes, i.e., 500, 350, 250, and 150, respectively). The scan rate is 50 mV/sec in 0.1 M phosphate buffered saline at a pH of 7.4. This charge storage capacity is much higher that the 25 $mC/cm^2$ achieved for either iridium oxide on a smooth surface or for activated iridium oxide. Higher charge storage capacity, for example, exceeding 25 $mC/cm^2$, on smooth electrodes results in cracks and delamination of the iridium oxide layer. The average rate of deposition for the electroplated iridium oxide is 3.4 $mC/cm^2$/min for constant voltage plating compared at 1.2 $mC/cm^2$/min pulsed voltage plating using 0.5 second pulses. The average rate of deposition for the electroplated iridium oxide is 3.4 $mC/cm^2$/min for constant voltage plating compared at 1.2 $mC/cm^2$/min pulsed voltage plating using 0.5 second pulses.

Figure 6:
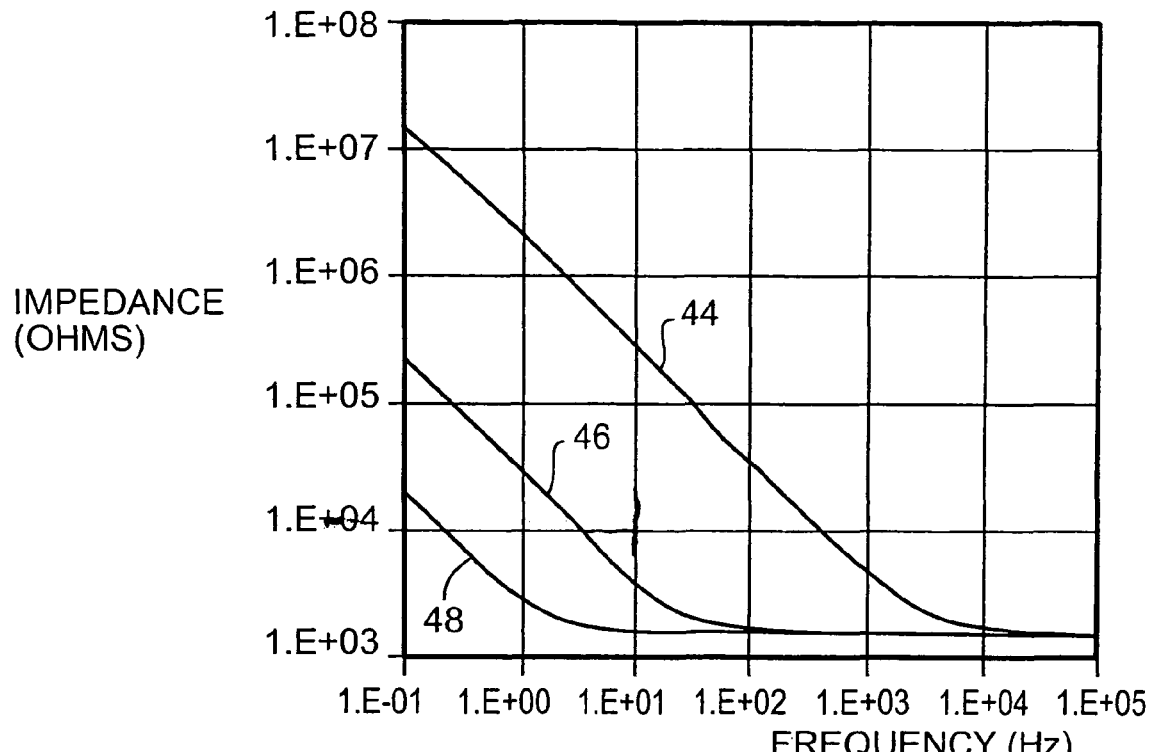
FIG. 6 is a plot of impedance as a function of frequency for select platinum samples.

FIG. 6 presents a comparison of the impedance spectra for three different surfaces: smooth platinum 44 before plating, after rough platinum 46 plating for 30 minutes, and after iridium oxide 48 plated on rough platinum, each having the same geometrical surface area of $20 \times 10^{-4}$ $cm^2$ for a polyimide array, where the plating was accomplished at +0.5V versus Ag/AgCl. The electrode impedance decreased after rough platinum plating and was further reduced after iridium oxide plating on the rough platinum surface. The charge storage capacity measured in the electrode's capacitance, which is proportional to the electrode surface area, was determined to increase more than 200 times for the iridium oxide plated surface, as compared with unplated electrodes of the same diameter. In an alternative embodiment, titanium nitride is coated on the rough platinum surface, preferably by sputtering deposition.

The iridium oxide plating solution is prepared as presented below.

Electrolyte Concentrations

| Chemical | Molecular Weight (g-mol) | Concentration | Quantity (milliMoles) |
|---|---|---|---|
| $IrCl_4$ | 334 | 1.42 g/l | 4.25 |
| $H_2O_2$ aqueous solution (30 wt %) | 34 | 10 ml/l | 88 |

-continued

| Chemical | Molecular Weight (g-mol) | Concentration | Quantity (milliMoles) |
|---|---|---|---|
| (COOH)$_2$ 2H$_2$O | 126 | 5 g/l | 40 |
| K$_2$CO$_3$ to pH 10.5 | 99 | ~34 g/l | 340 |

Solution Preparation

1. Dissolve 0.15 g iridium chloride hydrate in 100 ml deionized water, stirring for 30 minutes.
2. Add 1 ml aqueous hydrogen peroxide solution (30 weight percent), stirring for 10 minutes.
3. Add 0.5 g oxalic acid (COOH)$_2$ 2H$_2$O, stirring for 10 minutes.
4. Add anhydrous potassium carbonate to adjust the solution pH to 10.5.
5. Maintain the final solution at 100 to 25° C. for at least 2 days to stabilize.

Hydrogen peroxide enables oxide film deposition at lower current density. The complex of iridium salt with oxalic acid is believed to provide a stable solution for electrochemical oxidation of iridium to iridium oxide during electroplating and solution storage for about 3 months without precipitation of iridium oxide. The iridium oxide plating proceeds by the following reaction:

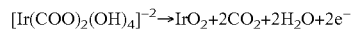

$$[Ir(COO)_2(OH)_4]^{-2} \rightarrow IrO_2 + 2CO_2 + 2H_2O + 2e^-$$

These procedures are presented in the following references, K. Yamanaka, "Anodically Electrodeposited Iridium Oxide Films (AEIROF) from Alkaline Solutions for Electrochromic Display Devices," Jpn. J. Appl. Phys. 28 632-37 (1989); R. D. Meyer, T. H. Nguyen, R. D. Rauh, and S. F. Cogan, "Electrodeposition of Iridium Oxide Charge Injection Electrodes," Proceeding of BMES/EMBS'99, Atlanta, Oct. 13-16, 1999; S. Marzouk, et al., "Electrodeposited Iridium Oxide pH Electrode for Measurement of Extracellular Myocardial Acidosis during Acute Ischemia," Anal. Chem., 70 5054-61 (1998).

EXAMPLE 1

An array with 16 platinum disks embedded in silicone rubber as electrodes was plated with iridium oxide. Each platinum disk had a diameter of 500 μm and had an exposed metal surface of 20×10$^{-4}$ cm$^2$. All the electrodes in the array were shorted to a common contact point for plating. The platinum disk electrodes were pulsed at 0.35 mC/cm$^2$, 1 ms biphasic square wave pulse at 50 Hz for 6 hours in saline. This stimulation removed surface contamination and polymer residue. The array was cleaned and electrochemically conditioned in 0.5 M H$_2$SO$_4$ solution by 10 cycles of voltage scans from −0.2V to +1.4V vs AgCl with 100 mV/sec scan rate. A thin layer of rough platinum (about 5 μm) was electroplated for 30 minutes on the platinum disk surface. Next, 10 cyclic voltammetric scans were carried out on the platinum surface in 4.25 mM iridium chloride solution to confirm the reduction and oxidation of iridium oxide. Then, iridium oxide was electroplated in the same solution at a constant voltage of +0.5 V as a function of AgCl for 25 minutes on the platinum surface. The resulting current density was determined to be 0.36 mA/cm$^2$. The iridium solution is purged with argon or nitrogen gas for 20-30 minutes prior to plating. A magnetic stirrer was used to agitate the solution during plating. The solution temperature was maintained at room temperature (i.e., about 22-24° C.). The resulting electrodes had very high capacitance, with an average of 15 mF/cm$^2$. The platinum disks had an average capacitance of 0.05 mF/cm$^2$, while the plated rough platinum surfaces had capacitance of 0.7 mF/cm$^2$.

EXAMPLE 2

A thin-film platinum polyimide array was used for iridium oxide plating. The array contained 16 electrodes of four different sizes, 500, 350, 250 and 150 μm diameter thin-film platinum disks, as exposed electrode surfaces. All of the electrodes in the array were shorted to common contact points for the plating. The platinum disk electrodes were first electrochemically cleaned by bubbling oxygen over the surface while the surface was held at +3V vs AgCl in 0.5 M H$_2$SO$_4$ for 5 sec. The surface was then cleaned by bubbling with hydrogen at −2.5V vs AgCl in 0.5 M H$_2$SO$_4$ for 5 seconds. This removed surface contamination and polymer residue. The array was electrochemically conditioned in 0.5 M H$_2$SO$_4$ solution by 10 cycles of voltage scans from −0.2V to +1.4V vs AgCl with 100 mV/sec scan rate. A thin layer of rough platinum (about 10 μm thick) was electroplated for 20 minutes on the platinum disk surface. Next, 10 cyclic voltammetric scans were carried out on the platinum surface in 4.25 mM iridium oxide solution to confirm the reduction and oxidation of iridium oxide peaks. Next, iridium oxide was electroplated on the platinum surface in the same solution at a constant voltage of +0.5V vs AgCl for 15 minutes. The resulting current density was measured as 0.27 mA/cm$^2$. The iridium solution was purged with argon or nitrogen gas for 20-30 minutes prior to plating. A magnetic stirrer agitated the solution during plating. The solution was maintained at room temperature (about 22° to 24° C.). The resulting electrode had very high capacitance with an average of 5.1 mF/cm$^2$. The thin-film platinum disks had an average capacitance of 0.023 mF/cm$^2$, while the rough platinum surfaces had an average capacitance of 0.96 mF/cm$^2$.

EXAMPLE 3

A thin-film platinum polyimide array was used for iridium oxide plating. The array contained 16 electrodes of 200 μm diameter thin film platinum disks as the exposed electrode surface. All the electrodes in the array were shorted to a common contact point for plating. The platinum disk electrodes were first electrochemically cleaned by bubbling oxygen on the surface at +3V vs AgCl in 0.5 M H$_2$SO$_4$ for 5 seconds. Then they were cleaned by bubbling hydrogen on the surface at −2.5V vs AgCl in 0.5 M H$_2$SO$_4$ for 5 seconds. This removed surface contamination and polymer residue. The array was electrochemically conditioned in 0.5 M H$_2$SO$_4$ solution by 10 cycles of voltage scans from −0.2V to +1.4V vs AgCl with a 100 mV/sec scan rate. A thin layer of platinum gray (about 10 μm thick) was electroplated for 20 minutes on the platinum disk surface. Next, an iridium layer was electrodeposited on the platinum gray surface. Finally, iridium was electrochemically activated to form iridium oxide by cyclic voltammetric scans within the potential window of −0.6V to +0.8V vs AgCl in saline. The solution was purged with argon or nitrogen gas for 20 to 30 minutes prior to iridium oxide activation. A magnetic stirrer agitated the solution during plating. The solution was maintained at 22° to 24° C.

In an alternative embodiment, iridium oxide is introduced during the platinum plating process such that the iridium oxide layer is deposited on the high surface area platinum gray to yield a gradient composition coating that varies approximately linearly from essentially pure platinum gray to essentially pure iridium oxide. It is clear that the gradient coating may vary in composition step-wise or in other than a non-linear manner. It is also clear that the composition need not be pure on either surface and that the gradient coating may equally well be comprised of a fraction of platinum and a complementary fraction of iridium oxide.

Figure 8:
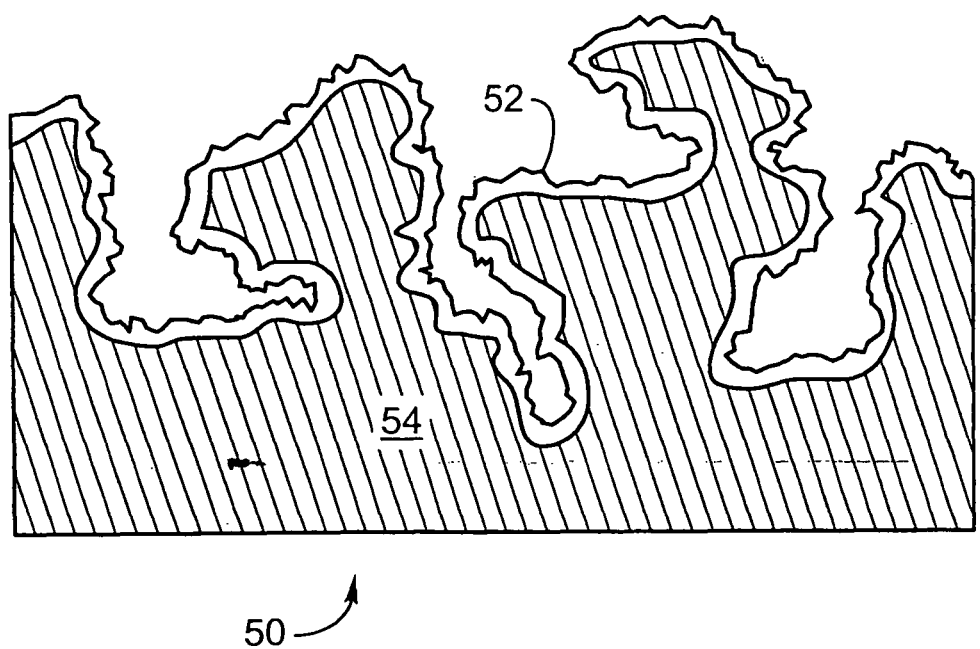
FIG. 8 is a schematic representation of a cross-section through a coated porous electrode.

Illustrated schematically in FIG. 8 is a cross section of a high surface area coated electrode, generally 50. The rough platinum electrode 54 is coated with a high surface area coating 52. The enhancement of the surface area of the rough platinum surface, which is preferably platinum gray, but which may be a chemically or mechanically roughened surface, is achieved by coating with the high surface area coating 52, which is preferably iridium oxide, but which in an alternative embodiment may be sputtered biocompatible material having a high surface area, such as titanium nitride.

Figure 9:
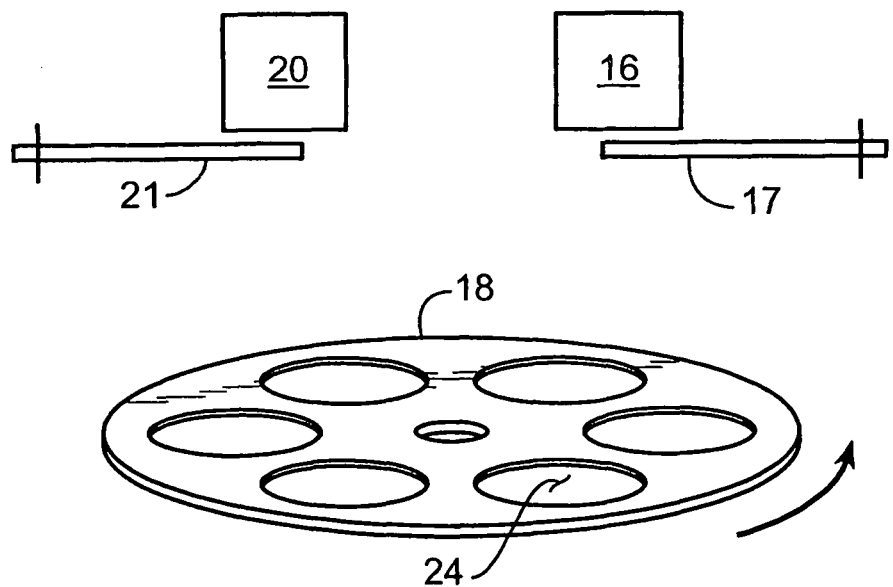
FIG. 9 illustrates a two-target sputtering apparatus.

A further alternative embodiment utilizes two-target sputtering for gradient coating deposition, generally illustrated in FIG. 9. The platinum and the iridium oxide are deposited by sequential graded co-sputtering. Sputtering is a relatively low-temperature method for fabricating an electrode 24 with two materials deposited in a gradient manner. This method creates an electrode 24 or electrode array that has platinum metal adjacent to the base of the electrode substrate, and iridium oxide at the surface of the electrode 24. The resulting structure is an approximately linear gradient from essentially pure platinum to essentially pure iridium oxide, although it is clear that the gradient coating may be started and/or terminated at any point in the gradient that is less than the essentially pure material. It is also to be understood that the gradient composition may vary in composition in a manner other than linearly. In alternative embodiments, the base of the electrode may be comprised of platinum gray, another metal, polymer, or ceramic. For neural stimulation, the preferred embodiment is a thin film flex circuit base made from a biocompatible material, such as polyimide, preferably with platinum or alternately with titanium conductive traces.

The electrode material gradient is sputtered such that the essentially pure platinum is deposited for about 300 to 3000 angstroms, although it is envisioned that the platinum layer may be microns thick in an alternative embodiment. The iridium oxide is phased in until approximately 50% platinum and 50% iridium is being deposited. Then the platinum flux is reduced until only iridium oxide is deposited, resulting in an electrode surface of 100% iridium oxide.

To achieve this sequential graded co-sputtering, the electrodes are preferably placed on a rotating carousel 18 in a sputtering machine that is capable of very rapid rotation and can sputter from two targets simultaneously. One target is an RF target for the sputtering of the iridium oxide. 20 An RF target is necessary as opposed to a DC target, since iridium oxide is a poor conductor. Since platinum is a good electrical conductor, the other target is preferably DC, although in alternative embodiments it may be RF. Rapid carousel rotation on the order of 100 rpm minimizes the layering effect of the sputtering deposition process. Each electrode passes the platinum sputtering target 16 and the iridium oxide sputtering target 20, alternately, in rapid succession, thereby forming a series of extremely thin alternating layers. Reducing the amount of deposited material to 10 to 40 angstroms per rotation yields a smoother gradient.

Deposition is preferably done with an argon background pressure of 1 to 10 mTorr. Initially only the platinum sputtering target 16 is powered. In the preferred embodiment, a very high power and high rate of deposition is used such that the platinum is deposited in a very rough film on the electrode 24, maximizing the surface area. However, after this rough base is achieved, power to the platinum sputtering target 16 is reduced to minimize the layering effect. Alternatively, a layer of platinum grey is plated on the electrode 24 prior to sputtering to provide a rough, high surface area base.

Then the iridium oxide target 20 is powered at a low level to begin introducing iridium oxide into the platinum deposition.

In yet another embodiment, the deposition rate of both target materials is modulated with shutters rather than by power modulation. Achieving deposition rate modulation requires an independent shutter for each target. The shutter 21 over the iridium oxide target is slowly opened while the shutter over the platinum target 17 is slowly closed resulting in a graded transition from platinum to iridium oxide. Near the end of the deposition process, the iridium oxide target shutter 21 is completely open and the platinum target shutter 17 is completely closed, resulting in pure iridium oxide at the electrode surface 24.

Since the simultaneous wet etching of platinum and iridium oxide is very difficult, the final steps in electrode fabrication preferably utilize the lift-off process for patterning the deposited material gradient.

An electrode 24 or electrode array having a gradient coating by this process has the excellent charge delivery properties possessed by iridium oxide while maintaining the robustness afforded by the underlying platinum layer.

Obviously, many modifications and variations of the present invention are possible in light of the above teachings. It is therefore to be understood that, within the scope of the appended claims, the invention may be practiced otherwise than as specifically described.

What is claimed is:

1. A dual coated high surface area implantable metal electrode comprising:
   a smooth metal substrate, suitable for implantation in an eye, having a first surface area and having a geometric shape;
   an electrically conductive coating comprised of fractal platinum and not platinum black or shiny platinum, deposited on said smooth metal substrate, suitable for implantation in an eye, having a second surface area,
   said electrically conductive coating having said second surface area greater than five times said first surface area of said smooth metal substrate; and
   a further protective fractal coating deposited on said electrically conductive coating, suitable for implantation in an eye.

2. The implantable electrode of claim 1, wherein said implantable metal electrode has a charge storage capacity that is greater than 35 mC/cm$^2$.

3. The implantable electrode of claim 1, wherein said further protective fractal coating is comprised of titanium nitride.

4. The implantable electrode of claim 3, wherein said titanium nitride is a sputtered coating.

5. The implantable electrode of claim 1, wherein said implantable metal electrode is suitable for a visual prosthesis.

6. The implantable electrode of claim 5, wherein said visual prosthesis is a retinal electrode array.

7. The implantable electrode of claim 1, wherein said surface coating is biocompatible.

8. The implantable electrode of claim 1, wherein said further protective fractal coating has a third surface area of between 5 and 500 times said the corresponding first surface area of said smooth metal substrate.

9. The implantable electrode of claim 1, wherein said further protective fractal coating has a thickness of at least 1 micrometer.

10. The implantable electrode of claim 1, wherein said further protective fractal coating is comprised of iridium oxide.

* * * * *